(12) United States Patent
Krishnan et al.

(10) Patent No.: US 8,446,584 B2
(45) Date of Patent: May 21, 2013

(54) RECONFIGURABLE SPECTROSCOPIC ELLIPSOMETER

(75) Inventors: Shankar Krishnan, Santa Clara, CA (US); Haiming Wang, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 265 days.

(21) Appl. No.: 13/106,940

(22) Filed: May 13, 2011

(65) Prior Publication Data

US 2012/0287433 A1  Nov. 15, 2012

(51) Int. Cl.
*G01J 4/00* (2006.01)

(52) U.S. Cl.
USPC .......................................... 356/369

(58) Field of Classification Search
USPC ...................... 356/369; 250/559.09
See application file for complete search history.

(56) References Cited

U.S. PATENT DOCUMENTS

| | | | |
|---|---|---|---|
| 5,298,973 A * | 3/1994 | Fukazawa et al. | 356/368 |
| 5,581,350 A | 12/1996 | Chen et al. | |
| 5,596,406 A | 1/1997 | Rosencwaig et al. | |
| 5,956,145 A | 9/1999 | Green et al. | |
| 6,583,875 B1 | 6/2003 | Wei et al. | |
| 6,734,968 B1 | 5/2004 | Wang et al. | |
| 7,633,625 B1 | 12/2009 | Woollam et al. | |

OTHER PUBLICATIONS

Hauge, "Mueller matrix ellipsometry with imperfect compensators," JOSA A 68(11), 1519-1528, 1978.
Azzam, "A simple Fourier photopolarimeter with rotating polarizer and analyzer for measuring Jones and Mueller matrices," Opt Comm 25(2), 137-140, 1978.
Aleksandrov, et. al. "Methods and apparatus for complete ellipsometry (review)," J Appl Spectroscopy 44(6), 559-578, 1986.

* cited by examiner

*Primary Examiner* — Roy M Punnoose
(74) *Attorney, Agent, or Firm* — Luedeka Neely Group, P.C.; Rick Barnes

(57) ABSTRACT

A Mueller ellipsometer of the type having a first rotating element on an incident beam side of a sample and a second rotating element on a reflected beam side of the sample and a detector having an integration time, having a controller for selectively and separately adjusting (1) a first angular frequency of the first rotating element and (2) a second angular frequency of the second rotating element.

8 Claims, 1 Drawing Sheet

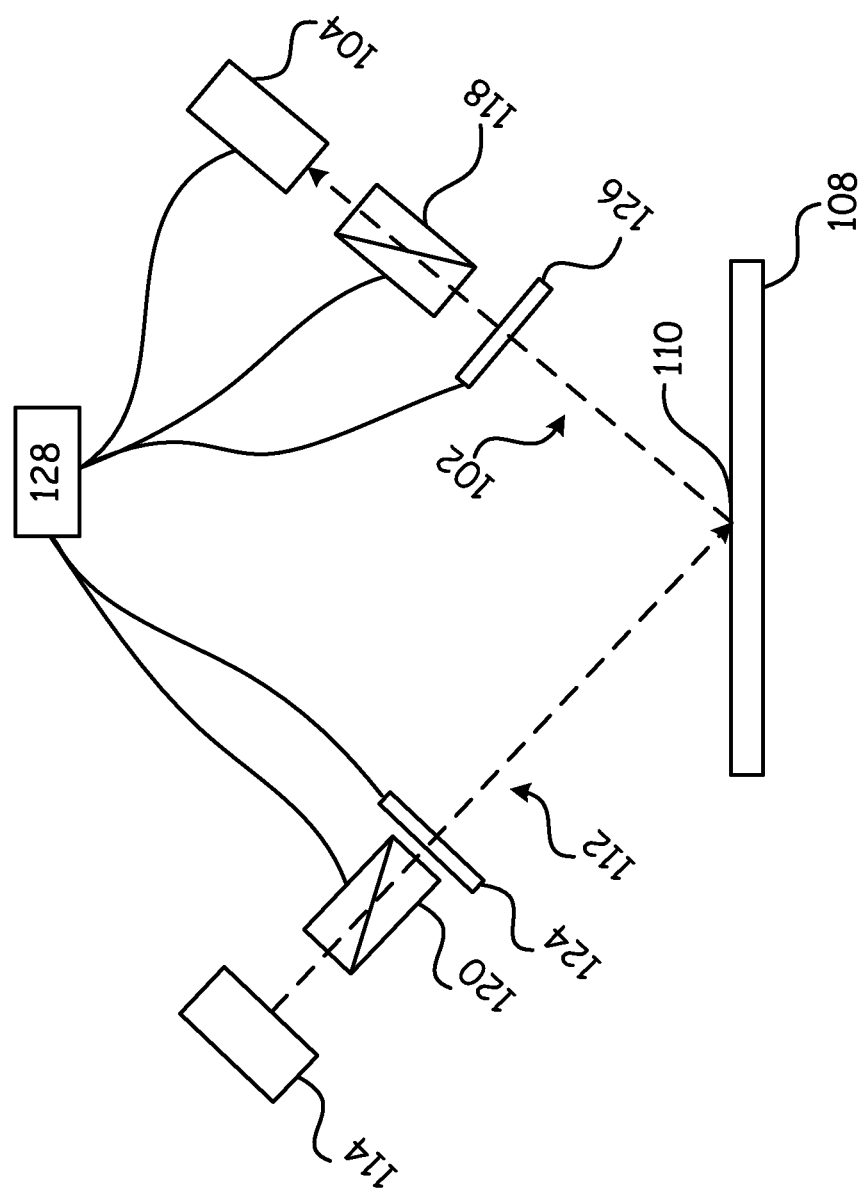

US 8,446,584 B2

RECONFIGURABLE SPECTROSCOPIC ELLIPSOMETER

FIELD

This invention relates to the field of spectroscopy. More particularly, this invention relates to measuring critical dimensions of integrated circuits using an adaptation of a Mueller ellipsometer.

INTRODUCTION

Spectroscopic ellipsometry is used extensively in integrated circuit metrology and process control, such as for measuring the thicknesses of film stacks and the critical dimensions of integrated circuit structures during etch, lithography, and other fabrication processes. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

One of the most critical challenges is the low sensitivity caused by the ever-reducing dimensions of the structures being measured. For example, the lateral dimensions of gate structures have been continuously reduced, typically down to a few tens of nanometers, while at the same time there remains a critical need to maintain extremely high measurement precision and tool-to-tool matching.

Mueller ellipsometry is often used, where the sample is described by a 4-by-4 matrix, where each of the elements in the matrix is a set of spectra.

Commonly-used ellipsometers include a light source that reflects a light beam off of a sample and into a detector. Between the light source and the sample there is a polarizer. Between the sample and the detector, there is an analyzer. Either or both of polarizer and the analyzer can rotate.

A rotating quarter-wave plate (or alternately a photoelastic modulator, acousto-optic modulator, liquid-crystal modulator, or other polarization-sensitive phase modulation means) is optionally placed between the sample and one or both of the polarizer and the analyzer. These elements are commonly called compensators. Typically, only one element on either side of the sample is rotated during a measurement.

Different ones of these configurations produce different numbers of harmonic spectra, where some produce a sufficient number of harmonic spectra to completely populate the Mueller matrix. However, additional improvements to a Mueller spectroscopic ellipsometer are desirable.

SUMMARY OF THE CLAIMS

The above and other needs are met by a Mueller ellipsometer of the type having a first rotating element on an incident beam side of a sample and a second rotating element on a reflected beam side of the sample and a detector having an integration time, having a controller for selectively and separately adjusting (1) a first angular frequency of the first rotating element and (2) a second angular frequency of the second rotating element.

In various embodiments, the first rotating element is a polarizer In other embodiments the first rotating element is a compensator disposed between a polarizer and the sample along the incident beam In some embodiments the second rotating element is an analyzer In other embodiments the second rotating element is a compensator disposed between the sample and the analyzer along the reflected beam In some embodiments the controller additionally selectively and separately adjusts the integration time In some embodiments the ellipsometer is a spectroscopic ellipsometer. In other embodiments the ellipsometer is an angle resolved ellipsometer.

BRIEF DESCRIPTION OF THE DRAWING

Further advantages of the invention are apparent by reference to the detailed description when considered in conjunction with the FIGURE, which is not to scale so as to more clearly show the details, wherein like reference numbers indicate like elements throughout the view, and which depicts a basic exemplary embodiment of a spectroscopic ellipsometer according to an embodiment of the present invention.

DETAILED DESCRIPTION

According to various embodiments of the present invention, there is provided an ellipsometer having two rotating polarizing elements (one on each side of the sample), where the angular frequencies of the two rotating polarizing elements are separately adjustable. These two parameters, coupled with the acquisition time of the detector that is integrating the signals, determines the magnitudes of the harmonics that are produced, and the degree to which the Mueller matrix is populated.

With reference now to the FIGURE, there is depicted a basic exemplary embodiment of a spectroscopic ellipsometer 100 for taking measurements at a position 110 on a sample 108. A broadband light source 114 produces an incident beam 112 that passes through a polarizer 120 and an optional compensator means 124, before acquiring the sample 108. The light reflected from the sample 108 comprises a reflected beam 102 that passes through optional compensator means 126 and analyzer 118 before attaining the detector 104. A controller 128 is operable to selectively adjust the angular frequencies of the appropriate one or more of the elements 120, 124, 126, and 118, and the integration time of the detector 104.

As an example, consider an ellipsometer where the polarizer and the analyzer rotate at frequencies $f_p$ and $f_a$ (in hertz) with angular frequencies of $[\omega_p, \omega_a]$, respectively. For a sample described by a Mueller matrix $M_{ij}$, i, j=0, 1, 2, 3, propagating the stokes vector from the light source to the detector yields the detector signal:

$$S_D = S_F \begin{bmatrix} f_0 + f_1\cos2(\omega_a - \omega_p)t + f_2\sin2(\omega_a - \omega_p)t + \\ f_3\cos2\omega_p t + f_4\cos2\omega_p t + f_5\cos2\omega_a t + f_6\sin2\omega_a t + \\ f_7\cos2(\omega_a + \omega_p)t + f_8\sin2(\omega_a + \omega_p)t \end{bmatrix}, \quad (1)$$

where the harmonic coefficients $f_n$, n=0, 1, . . . , 8 are directly related to the sample Mueller elements:

$$S_F = \frac{I_i}{4} \quad (2)$$

$$f_0 = M_{00}$$

$$f_1 = \frac{M_{11} + M_{22}}{2}$$

-continued $$f_2 = \frac{M_{12} - M_{21}}{2}$$

$$f_3 = M_{01}$$

$$f_4 = -M_{02}$$

$$f_5 = M_{10}$$

$$f_6 = -M_{20}$$

$$f_7 = \frac{M_{11} - M_{22}}{2}$$

$$f_8 = -\frac{M_{12} + M_{21}}{2}.$$

It is generally preferable to integrate the detector signal at a certain time period, accumulating all of the photons collected during this period of time, and recording the corresponding photoelectron signals as the so-called "sums." Various embodiments of the present invention use "32-sum," where for a data acquisition time of T, detector signals in each interval of T/32 are accumulated and recorded, as given by:

$$S_m = \int_{mT/32}^{(m+1)T/32} S_D(t)dt, \quad (3)$$

where m=0, 1, ..., 31. Defining the functions as:

$$\cos c(x, m) = \begin{cases} \frac{\cos mTx - \cos(m+1)Tx}{Tx}, & x \neq 0 \\ 1, & x = 0 \end{cases} \quad (4)$$

$$\sin c(x, m) = \begin{cases} -\frac{\sin mTx - \sin(m+1)Tx}{Tx}, & x \neq 0 \\ 1, & x = 0 \end{cases},$$

and applying equations (1) and (2) to equation (3) yields the sums of a rotating polarizer and analyzer configuration related to the sample and system characteristics, as:

$$G_{mn} = \frac{T}{32} \begin{bmatrix} 1, \sin c\left(\frac{\omega_a - \omega_p}{16}, m\right), \cos c\left(\frac{\omega_a - \omega_p}{16}, m\right), \sin c\left(\frac{\omega_p}{16}, m\right), \\ \cos c\left(\frac{\omega_p}{16}, m\right), \sin c\left(\frac{\omega_a}{16}, m\right), \cos c\left(\frac{\omega_a}{16}, m\right), \\ \sin c\left(\frac{\omega_a + \omega_p}{16}, m\right), \cos c\left(\frac{\omega_a + \omega_p}{16}, m\right) \end{bmatrix}^T \quad (5)$$

$$f_n = [f_0, f_1, f_2, f_3, f_4, f_5, f_6, f_7, f_8]^T,$$
$$m = 0, 2, \cdots, 31; \quad n = 0, 1, \cdots, 8 \quad S = Gf.$$

The linear equations Gf=S provides nine harmonic coefficients from 32 sums signals. This is an over-determined problem and one method to solve it is the so-called singular value decomposition method. Solutions of these linear equations indicate that the magnitudes of these harmonics are related to certain system parameters, namely, the angular frequencies and the acquisition time.

For example, a dual-rotating element ellipsometer having an acquisition time of one second is seen to exhibit different measurement capabilities (as measured by the standard deviation of repeated measurements), when using rotational frequencies of [2, 3] hertz in one case and [4, 5] hertz in another case for the polarizer and analyzer, respectively.

Which frequency pair, and the exact values of the desired frequencies, will differ according to the specific configuration of the ellipsometer (which elements are present and rotating, etc.) and the material and structure of the sample being measured.

The above method can be applied to other Mueller spectroscopic ellipsometers with dual rotating polarizing elements. For instance, for a dual rotating compensator ellipsometer, one can express the detector signal as 25 harmonics related to the rotating frequencies of the compensators in the illumination side ($\omega_g$) and in the analyzer side ($\omega_q$), as shown below:

$$S_D = S_F \begin{bmatrix} f_0 + f_1 \cos 2(\omega_g - \omega_q)t + f_2 \sin 2(\omega_g - \omega_q)t + \\ f_3 \cos 4(\omega_g - \omega_q)t + f_4 \sin 4(\omega_g - \omega_q)t + \\ f_5 \cos 2\omega_g t + f_6 \sin 2\omega_g t + f_7 \cos 2\omega_q t + f_8 \sin 2\omega_q t + \\ f_9 \cos(4\omega_g - 2\omega_q)t + f_{10} \sin(4\omega_g - 2\omega_q)t + \\ f_{11} \cos(2\omega_g - 4\omega_q)t + f_{12} \sin(2\omega_g - 4\omega_q)t + \\ f_{13} \cos 4\omega_g t + f_{14} \sin 4\omega_g t + f_{15} \cos 4\omega_q t + f_{16} \sin 4\omega_q t + \\ f_{17} \cos 2(\omega_g + \omega_q)t + f_{18} \sin 2(\omega_g + \omega_q)t + \\ f_{19} \cos(4\omega_g + 2\omega_q)t + f_{20} \sin(4\omega_g + 2\omega_q)t + \\ f_{21} \cos(2\omega_g + 4\omega_q)t + f_{22} \sin(2\omega_g + 4\omega_q)t + \\ f_{23} \cos 4(\omega_g + \omega_q)t + f_{24} \sin 4(\omega_g + \omega_q)t \end{bmatrix}. \quad (6)$$

Similarly, one can relate these harmonic coefficients to 32-sum:

$$G_{mn} = \frac{T}{32} \begin{bmatrix} 1, \sin c\left(\frac{\omega_g - \omega_q}{16}, m\right), \cos c\left(\frac{\omega_g - \omega_q}{16}, m\right), \\ \sin c\left(\frac{\omega_g - \omega_q}{8}, m\right), \cos c\left(\frac{\omega_g - \omega_q}{8}, m\right), \sin c\left(\frac{\omega_g}{16}, m\right), \\ \cos c\left(\frac{\omega_g}{16}, m\right), \sin c\left(\frac{\omega_q}{16}, m\right), \cos c\left(\frac{\omega_q}{16}, m\right), \\ \sin c\left(\frac{2\omega_g - \omega_q}{16}, m\right), \cos c\left(\frac{2\omega_g - \omega_q}{16}, m\right), \\ \sin c\left(\frac{\omega_g - 2\omega_q}{16}, m\right), \cos c\left(\frac{\omega_g - 2\omega_q}{16}, m\right), \\ \sin c\left(\frac{\omega_g}{8}, m\right), \cos c\left(\frac{\omega_g}{8}, m\right), \\ \sin c\left(\frac{\omega_q}{8}, m\right), \cos c\left(\frac{\omega_q}{8}, m\right), \\ \sin c\left(\frac{\omega_g + \omega_q}{16}, m\right), \cos c\left(\frac{\omega_g + \omega_q}{16}, m\right), \\ \sin c\left(\frac{2\omega_g + \omega_q}{16}, m\right), \cos c\left(\frac{2\omega_g + \omega_q}{16}, m\right), \\ \sin c\left(\frac{\omega_g + 2\omega_q}{16}, m\right), \cos c\left(\frac{\omega_g + 2\omega_q}{16}, m\right), \\ \sin c\left(\frac{\omega_g + \omega_q}{8}, m\right), \cos c\left(\frac{\omega_g + \omega_q}{8}, m\right) \end{bmatrix}^T \quad (7)$$

$$f_n = [f_0, f_1, f_2, f_3, f_4, f_5, f_6, f_7, f_8, f_9, f_{10}, f_{11}, f_{12},$$
$$f_{13}, f_{14}, f_{15}, f_{16}, f_{17}, f_{18}, f_{19}, f_{20}, f_{21}, f_{22}, f_{23}, f_{24}]^T,$$
$$m = 0, 2, \cdots, 31; \quad n = 0, 1, \cdots, 24 \quad S = Gf$$

The linear equations Gf=S determine 25 harmonic coefficients from 32 sums signals. This is an over-determined problem and again, one method to solve it is the singular value decomposition method. Solutions of these linear equations indicate that the magnitudes of these harmonics are related to certain system parameters, namely, the angular frequencies and the acquisition time.

Similarly, for the various other dual-rotating element embodiments, one can simply apply the same method to relate the harmonic coefficients to the 32-sum, and find that the harmonic coefficients can be advantageously reconfigured by changing the rotation frequencies and the integration time. As further example, a rotating compensator—rotating analyzer system produces fifteen harmonics, as given by:

$$S_D = S_F \begin{bmatrix} f_0 + f_1\cos2(\omega_a - \omega_p)t + f_2\sin2(\omega_a - \omega_p)t + \\ f_3\cos(2\omega_a - 4\omega_p)t + f_4\sin(2\omega_a - \omega_p)t + \\ f_5\cos2\omega_p t + f_6\sin2\omega_p t + f_7\cos2\omega_a t + f_8\sin2\omega_a t + \\ f_9\cos2(\omega_a + \omega_p)t + f_{10}\sin2(\omega_a + \omega_p)t + \\ f_{11}\cos4\omega_p t + f_{12}\sin4\omega_p t + \\ f_{13}\cos(2\omega_a + 4\omega_p)t + f_{14}\sin(2\omega_a + 4\omega_p)t \end{bmatrix}. \quad (8)$$

The relation between the harmonic coefficients and the 32-sum can be determined in a similar way as:

$$G_{mn} = \frac{T}{32} \begin{bmatrix} 1, \operatorname{sinc}\left(\frac{\omega_a - \omega_g}{16}, m\right), \operatorname{cosc}\left(\frac{\omega_a - \omega_g}{16}, m\right), \\ \operatorname{sinc}\left(\frac{\omega_a - 2\omega_g}{16}, m\right), \operatorname{cosc}\left(\frac{\omega_a - \omega_g}{16}, m\right), \operatorname{sinc}\left(\frac{\omega_p}{16}, m\right), \\ \operatorname{cosc}\left(\frac{\omega_p}{16}, m\right), \operatorname{sinc}\left(\frac{\omega_a}{16}, m\right), \operatorname{cosc}\left(\frac{\omega_a}{16}, m\right), \\ \operatorname{sinc}\left(\frac{\omega_a + \omega_g}{16}, m\right), \operatorname{cosc}\left(\frac{\omega_a + \omega_g}{16}, m\right), \\ \operatorname{sinc}\left(\frac{\omega_p}{8}, m\right), \operatorname{cosc}\left(\frac{\omega_p}{8}, m\right), \\ \operatorname{sinc}\left(\frac{\omega_a + 2\omega_p}{16}, m\right), \operatorname{cosc}\left(\frac{\omega_a + 2\omega_p}{16}, m\right) \end{bmatrix}^T \quad (9)$$

$$f_n = [f_0, f_1, f_2, f_3, f_4, f_5, f_6, f_7, f_8, f_9, f_{10}, f_{11}, f_{12}, f_{13}, f_{14}]^T,$$
$$m = 0, 2, \cdots, 31; \quad n = 0, 1, \cdots, 14 \quad S = Gf$$

For a rotating polarizer—rotating compensator system, the above harmonic analysis still applies, one just needs to exchange frequencies $\omega_a$ and $\omega_p$ in equations (6) and (7). Finally, for a system with rotating compensators on both sides of the sample, one will obtain 25 harmonics, and can apply equations (6) and (7) to relate 32-sum to harmonic coefficients, as already described.

It is noted that in the above three embodiments, even though one can get fifteen to twenty-five harmonics, one can still only measure nine Mueller elements. All the methods described and contemplated herein can be applied to both spectroscopic and angle-resolved systems. In a basic embodiment, one method identifies the harmonic or harmonics with the highest sensitivity for the system and sample combination. This harmonic or these harmonics are identified as the optimum harmonic or harmonics, and the angular frequencies of the rotating elements are adjusted accordingly, to enhance the optimum harmonic or harmonics. The angular frequency and the integration time can be adjusted in the system 100 either by user input as determined such as by empirically or modeled, or automatically such as by system 100 configuration.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. In a Mueller ellipsometer of the type having a first rotating element on an incident beam side of a sample and a second rotating element on a reflected beam side of the sample and a detector having an integration time, the improvement comprising a controller for selectively and separately adjusting (1) a first angular frequency of the first rotating element and (2) a second angular frequency of the second rotating element.

2. The ellipsometer of claim 1, wherein the first rotating element is a polarizer.

3. The ellipsometer of claim 1, wherein the first rotating element is a compensator disposed between a polarizer and the sample along the incident beam.

4. The ellipsometer of claim 1, wherein the second rotating element is an analyzer.

5. The ellipsometer of claim 1, wherein the second rotating element is a compensator disposed between the sample and the analyzer along the reflected beam.

6. The ellipsometer of claim 1, wherein the controller additionally selectively and separately adjusts the integration time.

7. The ellipsometer of claim 1, wherein the ellipsometer is a spectroscopic ellipsometer.

8. The ellipsometer of claim 1, wherein the ellipsometer is an angle resolved ellipsometer.

* * * * *